(12) United States Patent
Devengenzo et al.

(10) Patent No.: US 7,955,322 B2
(45) Date of Patent: Jun. 7, 2011

(54) WIRELESS COMMUNICATION IN A ROBOTIC SURGICAL SYSTEM

(75) Inventors: Roman L. Devengenzo, Sunnyvale, CA (US); Alan Loh, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 964 days.

(21) Appl. No.: 11/613,915

(22) Filed: Dec. 20, 2006

(65) Prior Publication Data

US 2007/0137372 A1 Jun. 21, 2007

Related U.S. Application Data

(60) Provisional application No. 60/752,755, filed on Dec. 20, 2005.

(51) Int. Cl.
*A61B 17/00* (2006.01)

(52) U.S. Cl. .......................... 606/1; 606/130; 74/490.01

(58) Field of Classification Search .............. 606/1, 130; 33/503; 74/490.01
See application file for complete search history.

(56) References Cited

U.S. PATENT DOCUMENTS

| | | | |
|---|---|---|---|
| 3,391,804 A * | 7/1968 | Flatau | 414/680 |
| 5,931,832 A | 8/1999 | Jensen | |
| 5,970,980 A * | 10/1999 | Adair | 128/849 |
| 6,222,699 B1 * | 4/2001 | Luffel et al. | 360/92.1 |
| 6,246,200 B1 | 6/2001 | Blumenkranz | |
| 6,331,181 B1 | 12/2001 | Tierney | |
| 6,491,701 B2 | 12/2002 | Tierney | |
| 6,770,081 B1 | 8/2004 | Cooper | |
| 7,338,434 B1 * | 3/2008 | Haarstad et al. | 600/37 |
| 7,727,185 B2 * | 6/2010 | Weitzner et al. | 604/95.01 |
| 2002/0072736 A1 * | 6/2002 | Tierney et al. | 606/1 |
| 2003/0004609 A1 * | 1/2003 | Canaday et al. | 700/245 |
| 2003/0216715 A1 * | 11/2003 | Moll et al. | 606/1 |
| 2004/0106916 A1 * | 6/2004 | Quaid et al. | 606/1 |
| 2005/0166413 A1 * | 8/2005 | Crampton | 33/503 |
| 2006/0020167 A1 * | 1/2006 | Sitzmann | 600/173 |
| 2006/0161138 A1 | 7/2006 | Orban | |
| 2006/0167440 A1 | 7/2006 | Cooper | |
| 2006/0235436 A1 | 10/2006 | Anderson | |
| 2007/0239105 A1 * | 10/2007 | Weitzner et al. | 604/95.01 |
| 2007/0276250 A1 * | 11/2007 | Donaldson | 600/459 |

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.
U.S. Appl. No. 11/613,695, filed Dec. 20, 2006, Devengenzo.
U.S. Appl. No. 11/556,484, filed Nov. 3, 2006, Devengenzo.
U.S. Appl. No. 11/613,800, filed Dec. 20, 2006, Devengenzo.
U.S. Appl. No. 11/240,087, filed Sep. 30, 2005, Anderson.
U.S. Appl. No. 11/613,578, filed Dec. 20, 2006, Devengenzo.
U.S. Appl. No. 60/752,755, filed Dec. 20, 2005, Devengenzo.
U.S. Appl. No. 11/240,113, filed Sep. 30, 2005, Moll.

* cited by examiner

*Primary Examiner* — Henry M Johnson, III
*Assistant Examiner* — Jeffrey B Lipitz

(57) ABSTRACT

In one embodiment, an insertion axis of a robotic manipulator is provided, the insertion axis including a base link operably coupled to a distal end of a manipulator arm, and a carriage link movably coupled to the base link along a lengthwise axis, the carriage link including a remote printed circuit assembly and transceiver for wirelessly communicating with a main printed circuit assembly external to the insertion axis. A robotic surgical system including such an insertion axis and a method for wireless communication in the system are also provided.

19 Claims, 11 Drawing Sheets

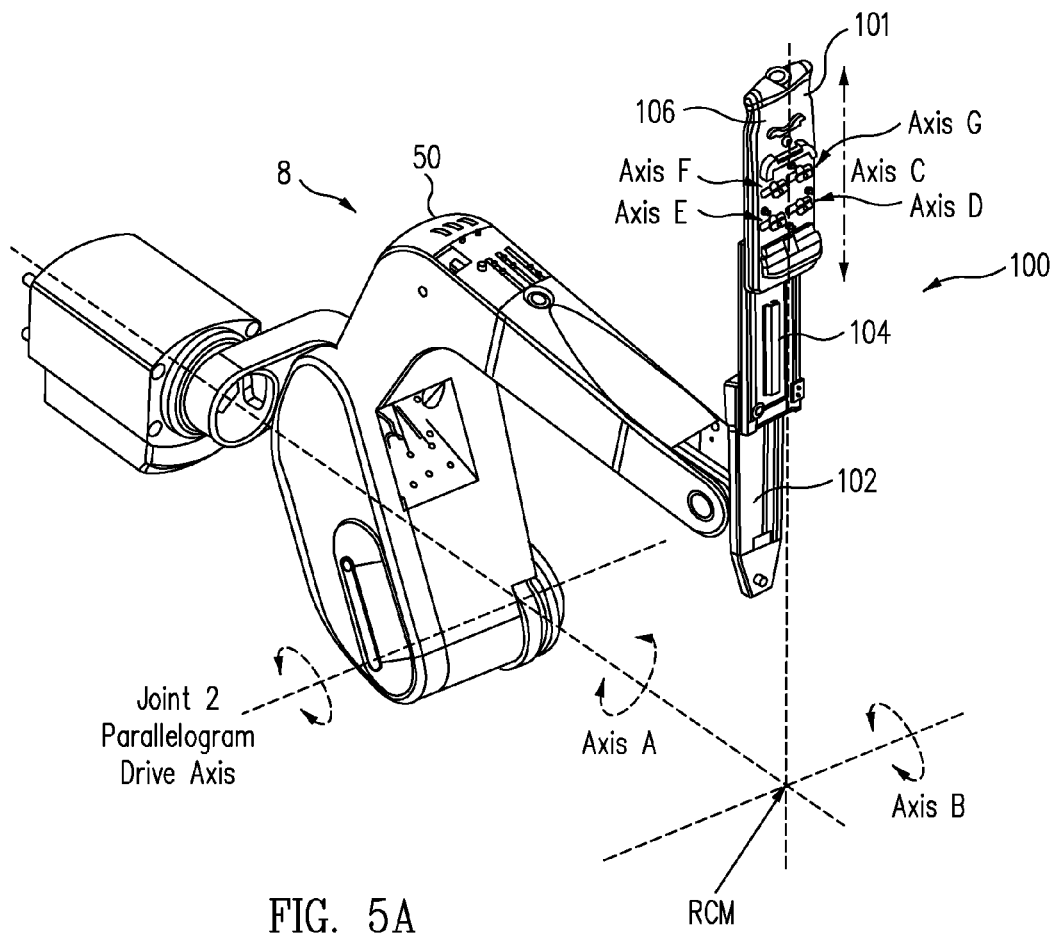
FIG. 5A
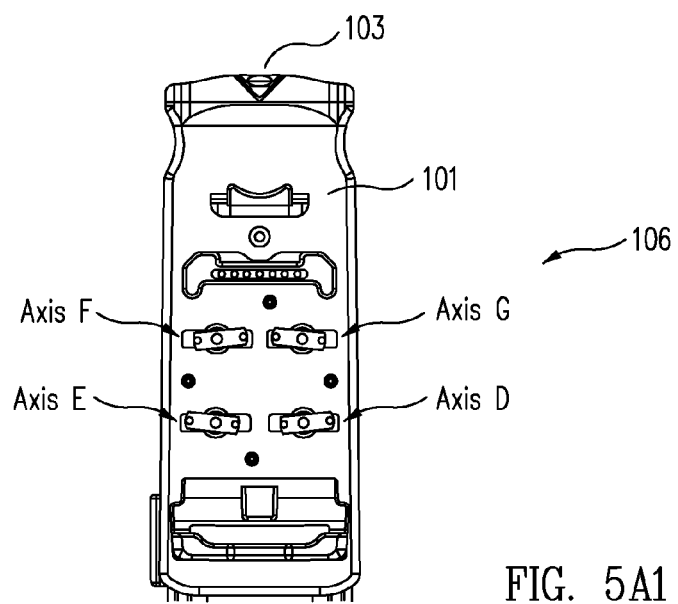
FIG. 5A1

WIRELESS COMMUNICATION IN A ROBOTIC SURGICAL SYSTEM

CROSS-REFERENCE TO RELATED APPLICATIONS

This application claims the benefit of U.S. Provisional Application Ser. No. 60/752,755, filed Dec. 20, 2005, the full disclosure of which (including all references incorporated by reference therein) is incorporated by reference herein for all purposes.

This application is related to U.S. application Ser. No. 11/613,578, filed Dec. 20, 2006, entitled "Cable Tensioning A Robotic Surgical System", U.S. application Ser. No. 11/613,800, filed Dec. 20, 2006, entitled "Telescopic Insertion Axis Of A Robotic Surgical System", U.S. application Ser. No. 11/556,484, filed Nov. 3, 2006, entitled "Indicator For Tool State and Communication In A Multi-Arm Robotic Telesurgery", and U.S. application Ser. No. 11/613,695, filed Dec. 20, 2006, entitled "Instrument Interface In A Robotic Surgical System", the full disclosures of which (including all references incorporated by reference therein) are incorporated by reference herein for all purposes.

TECHNICAL FIELD

The present invention relates generally to surgical robot systems and, more particularly, to an apparatus, system, and method for wireless communication and power supply in a robotic surgical system.

BACKGROUND

Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically assisted surgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instruments' position, orientation, and articulation at the surgical site. The slave is an electro-mechanical assembly that includes a plurality of arms, joints, linkages, servo-motors, etc. that are connected together to support and control the surgical instruments. In a surgical procedure, the surgical instruments (including an endoscope) may be introduced directly into an open surgical site or more typically through trocar sleeves into a body cavity. Depending on a surgical procedure, there are available a variety of surgical instruments, such as tissue graspers, needle drivers, electrosurgical cautery probes, etc., to perform various functions for the surgeon, e.g., holding or driving a needle, suturing, grasping a blood vessel, or dissecting, cauterizing or coagulating tissue.

A surgical manipulator assembly may be said to be divided into three main components that include a non-sterile drive and control component, a sterilizable end effector or surgical tool/instrument, and an intermediate connector component. The intermediate connector component includes mechanical elements for coupling the surgical tool with the drive and control component, and for transferring motion from the drive component to the surgical tool. Electrical cables, such as flexible flat cables, have been previously used to provide power, ground, and/or data signals between the components of the surgical system. Prior telerobotic surgical systems with such electrical cables are described for example in U.S. application Ser. No. 11/613,800, filed Dec. 20, 2006, entitled "Telescopic Insertion Axis Of A Robotic Surgical System", the complete disclosure of which has been previously incorporated herein by reference for all purposes. However, issues related to small clearances, electrical noise, mechanical fatigue, and mechanical hazards have caused a greater likelihood of malfunction and decreased system robustness. Furthermore, power and data transactions for electrical circuits must cross a sterile barrier (e.g., a membrane or film) that separates the sterile field containing surgical activity from the non-sterile mechanisms of the surgical robot.

What is needed, therefore, are improved apparatus and methods for providing electrical signals and power in a telerobotic surgical system for remotely interfacing to surgical instruments and the associated user interface controls and indicators at a surgical site on a patient.

SUMMARY

The present invention provides an advantageous apparatus, system, and method for wireless communication and power supply in a telerobotic surgical system.

In accordance with an embodiment of the present invention, an insertion axis of a robotic manipulator is provided, comprising a base link operably coupled to a distal end of a manipulator arm, and a carriage link movably coupled to the base link along a lengthwise axis, the carriage link including a remote printed circuit assembly and transceiver for wirelessly communicating with a main printed circuit assembly external to the insertion axis.

In accordance with another embodiment of the present invention, a robotic surgical system is provided, the system comprising the insertion axis described above, a manipulator arm including a main printed circuit assembly and transceiver, and an instrument coupled to the carriage link via an instrument interface.

In accordance with another embodiment of the present invention, a method of wireless communication in a robotic surgical system is provided, the method comprising providing a manipulator arm including a main printed circuit assembly and transceiver, providing an insertion axis as described above operably coupled to a distal end of the manipulator arm, and transmitting data wirelessly from a remote printed circuit assembly to a main printed circuit assembly.

Advantageously, the present invention allows for the substantial elimination of electrical wires through the insertion axis of the manipulator, thereby enabling the surgical manipulator to be made smaller and perform with greater robustness. Furthermore, separation of the electrical circuits provides a barrier to leakage currents that might otherwise cause electrical harm to patients and/or medical staff.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 5A through 5E illustrate perspective views and a partial frontal view of a manipulator including a telescopic insertion axis and wireless communication means in accordance with an embodiment of the present invention. FIG. 5A1 is a close-up view of a carriage link of the telescopic insertion axis in accordance with an embodiment of the present invention.

Figure 1:
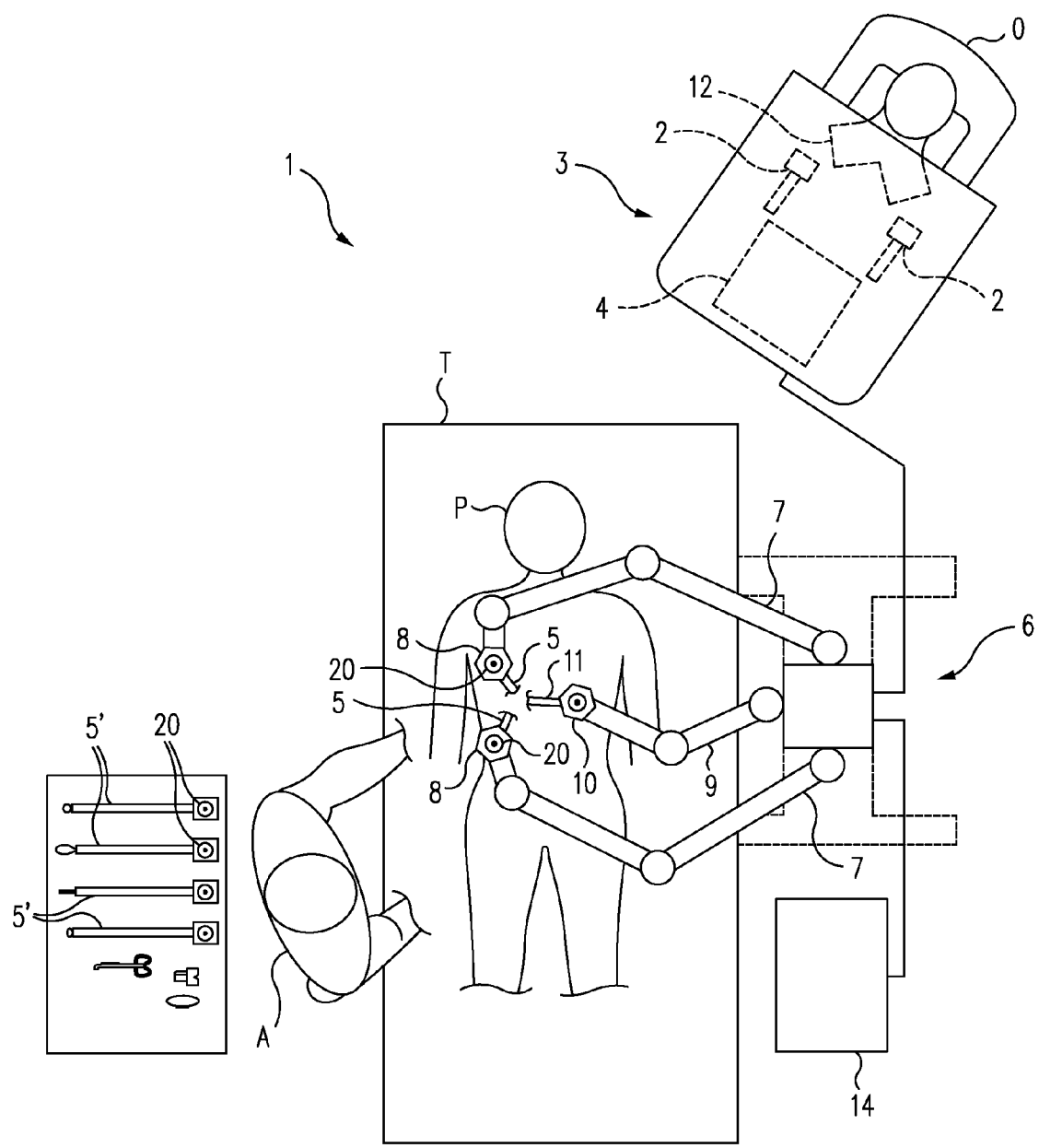
FIG. 1 is a schematic plan view of a portion of an operating theater illustrating a robotic surgical system, including a master surgeon console or workstation for inputting a surgical procedure and a robotic manipulator system for robotically moving surgical instruments at a surgical site within a patient.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a system, apparatus, and method for wireless communication in a telerobotic surgical system for performing robotically-assisted surgical procedures on a patient, particularly including neurosurgical procedures, such as stereotaxy, and endoscopic procedures, such as laparoscopy, arthroscopy, thoracoscopy and the like. The apparatus and method of the present invention is particularly useful as part of a telerobotic surgical system that allows the surgeon to manipulate the surgical instruments through a servomechanism at a location remote from the patient. One example of a robotic surgical system is the da Vinci® S™ surgical system available from Intuitive Surgical, Inc. of Sunnyvale, Calif. A User's Guide for the da Vinci® S™ surgical system is available from Intuitive Surgical, Inc. and is incorporated by reference herein for all purposes.

Figure 2A:
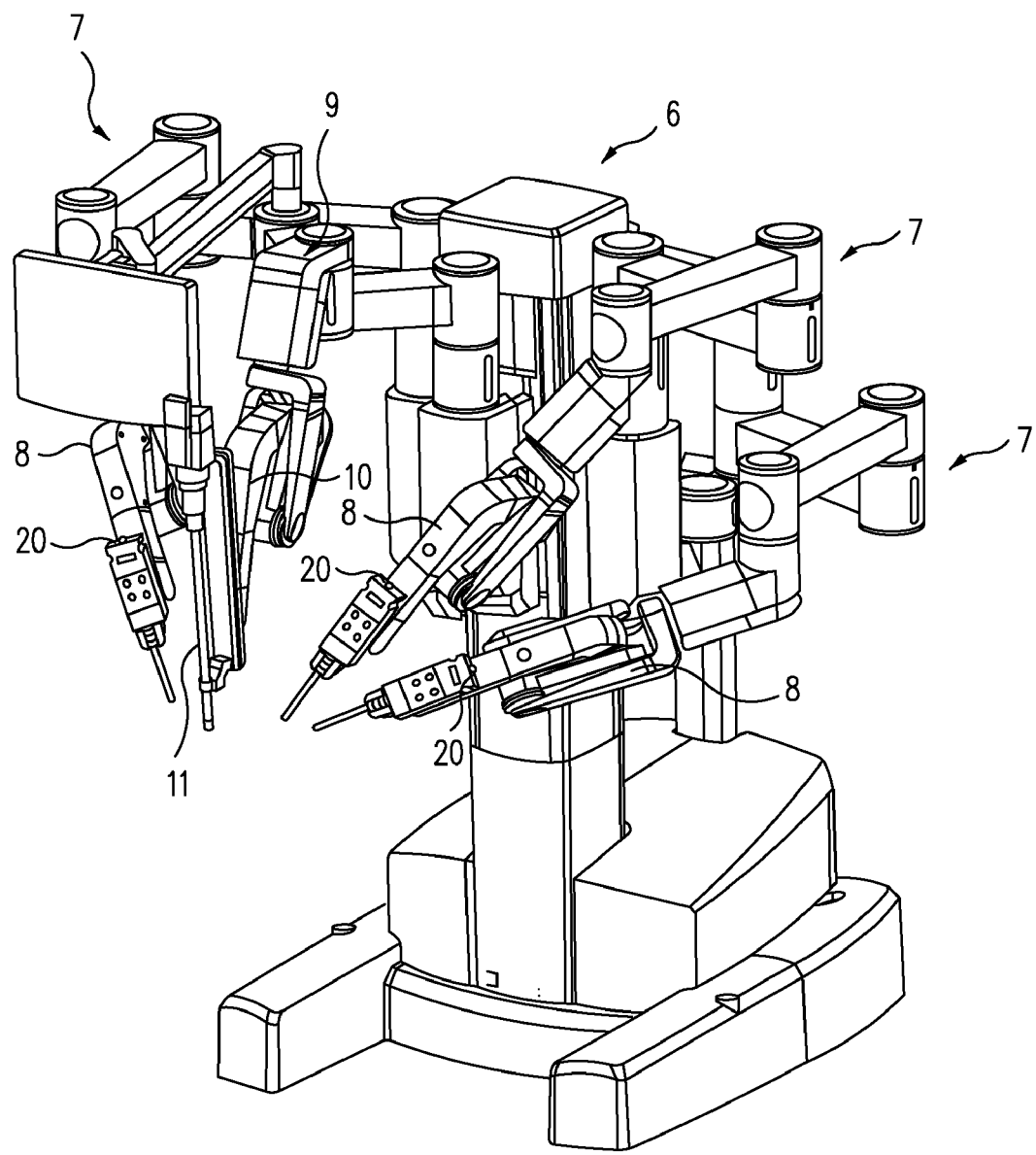
FIGS. 2A and 2B illustrate a perspective view and a front view, respectively, of an embodiment of a manipulator system, including positioning linkages or set up joints which allow a patient side robotic manipulator and/or an endoscope or camera robotic manipulator to be pre-configured for surgery.
Figure 2B:
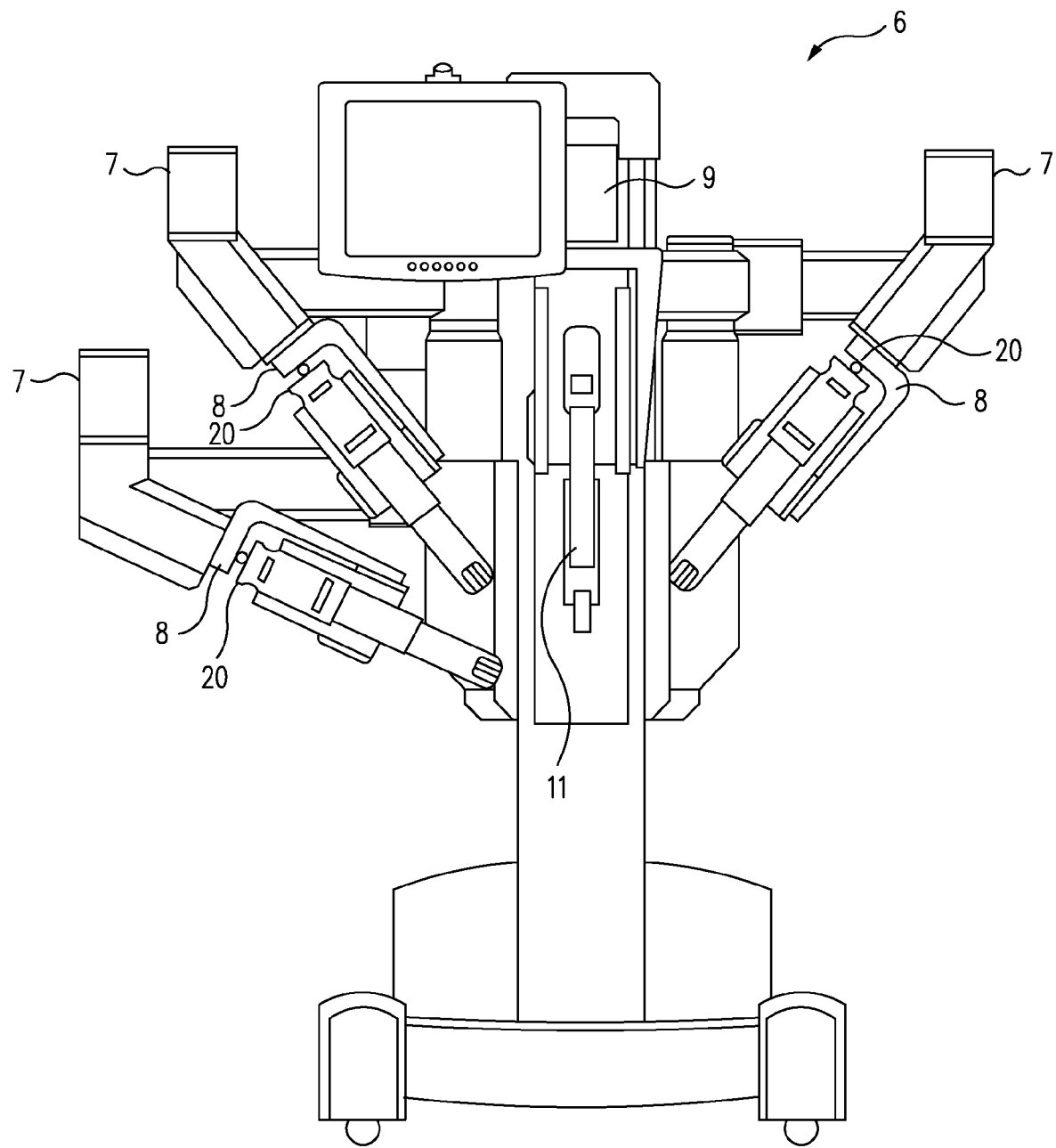
Figure 3:
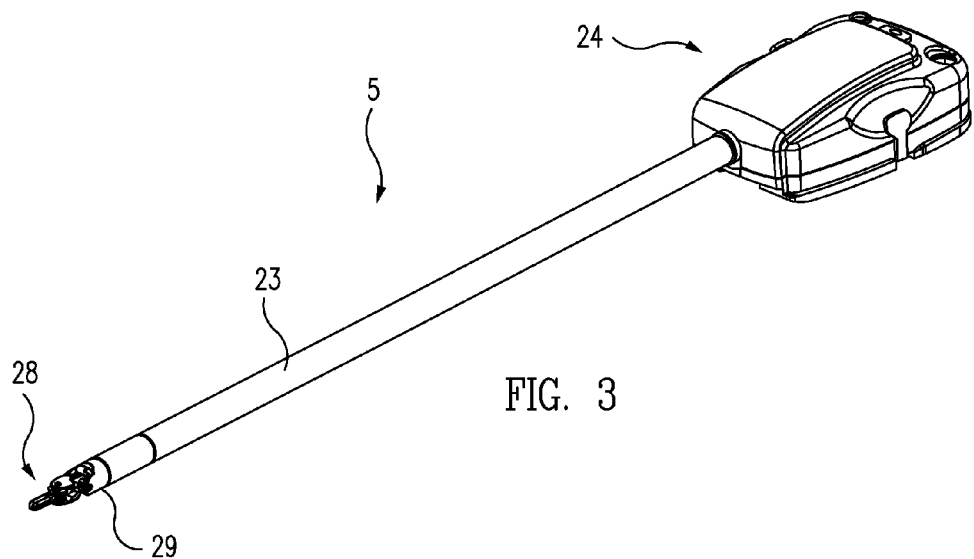
FIG. 3 is a perspective view of an example of a surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclosure of which is incorporated herein by reference. A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servomechanical movement of the instruments via a robotic patient-side manipulator system 6 (a cart-based system in this example) including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 1, the processor may comprise a number of data processing circuits (e.g., on the surgeon's console 3 and/or on the patient-side manipulator system 6), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, processor 4 may support wireless communication protocols such as Bluetooth, IrDA, HomeRF, IEEE 802.11, DECT, and Wireless Telemetry.

In one example, manipulator system 6 includes at least four robotic manipulator assemblies. Three linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm".

In one example, the image of the internal surgical site is shown to operator O by a stereoscopic display 12 in surgeon's console 3. The internal surgical site is simultaneously shown to assistant A by an assistance display 14.

Assistant A assists in pre-positioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A.

Some of the manipulators include a telescopic insertion axis 100 (FIGS. 5A-5E) in accordance with an embodiment of the present invention, although in other embodiments, all of the manipulators may include a telescopic insertion axis 100. Telescopic insertion axis 100 allows for movement of mounted instrument 5, via three operably coupled links, in one example.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Instruments 5 and endoscope 11 may be manually positioned when setting up for a surgical procedure, when reconfiguring the manipulator system 6 for a different phase of a surgical procedure, when removing and replacing an instrument with an alternate instrument 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 103 in FIGS. 5A-5D), or some other component to the manipulator assembly, thereby allowing assistant A to change the manipulator mode. In accordance with an embodiment of the present invention, signals for mode change may be passed wirelessly as discussed in greater detail below.

As can be seen in FIGS. 1 and 2A through 2B, indicators 20 are disposed on each manipulator assembly. In this embodiment, indicators 20 are disposed on manipulators 8, 10 near the interface between the manipulators and their mounted tools 5. In alternative embodiments, indicators 20 may instead be disposed elsewhere on manipulators 8, 10, or the like, with the indicators preferably being sufficiently close to the tools so that a signal generated by a particular indicator can be readily associated with a particular tool when the signal is viewed by assistant A. So as to unambiguously identify a tool 5 to be replaced by assistant A, system operator O may input a command into workstation 3 so that indicator 20 on the manipulator assembly associated with the specific tool 5 generates a visually identifiable signal that can be viewed by the assistant. An example of an indicator is disclosed in U.S. application Ser. No. 11/556,484, filed Nov. 3, 2006, the full disclosure of which (including all references incorporated by reference therein) is incorporated by reference herein for all purposes. Again, in accordance with an embodiment of the present invention, LED control signals for indicators 20 may be passed wirelessly as discussed in greater detail below.

FIG. 3 illustrates a perspective view of an articulated surgical tool or instrument 5. Tool 5 has a proximal housing 24 which interfaces with a tool holder or instrument interface of the manipulator, generally providing a quick release mounting engagement through a sterile adapter or interface, an example of which is disclosed in U.S. patent application Ser. No. 11/314,040, filed Dec. 20, 2005, now U.S. Pat. No. 7,666, 191, and U.S. patent application Ser. No. 11/395,418, filed Mar. 31, 2006, now U.S. Pat. No. 7,699,855, which are incorporated by reference herein for all purposes. Tool 5 includes an elongated shaft 23 supporting an end effector 28 relative to proximal housing 24. Proximal housing 24 accepts and transmits drive signals or drive motion between the manipulator 8 and the end effector 28. An articulated wrist 29 may provide two degrees of freedom of motion between end effector 28 and shaft 23, and the shaft may be rotateable relative to proximal housing 24 about the axis of the shaft so as to provide the end effector 28 with three orientational degrees of freedom within the patient's body.

The surgical tool may include a variety of articulated end effectors, such as jaws, scissors, graspers, needle holders, micro-dissectors, staple appliers, tackers, suction irrigation tools, and clip appliers, that may be driven by wire links, eccentric cams, push-rods, or other mechanisms. In addition, the surgical tool may comprise a non-articulated instrument, such as cutting blades, probes, irrigators, catheters or suction orifices. Alternatively, the surgical tool may comprise an electrosurgical probe for ablating, resecting, cutting or coagulating tissue. Examples of applicable adaptors, tools or instruments, and accessories are described in U.S. Pat. Nos. 6,331, 181, 6,491,701, and 6,770,081, the full disclosures of which (including disclosures incorporated by reference therein) are incorporated by reference herein for all purposes. Applicable surgical instruments are also commercially available from Intuitive Surgical, Inc. of Sunnyvale, Calif.

Figure 4:
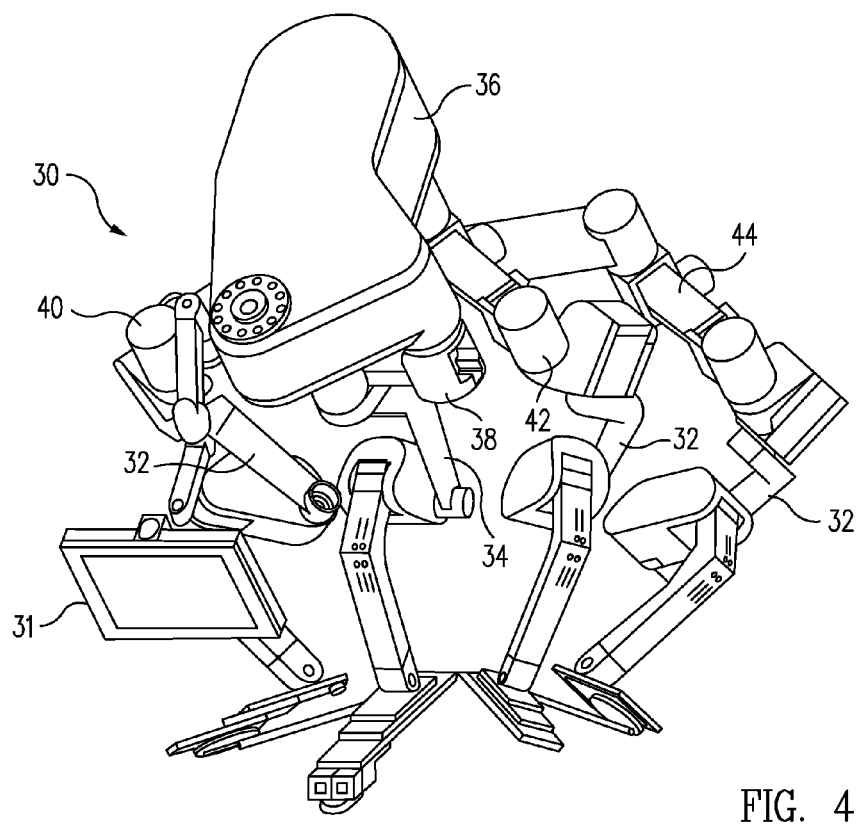
FIG. 4 is a perspective view from above of an alternative manipulator system including a plurality of positioning linkages, each supporting a manipulator arm.

Referring now to FIG. 4, a perspective view is illustrated of an alternative modular manipulator support assembly 30 that may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 that may be coupled to the orienting platform. Each arm movably supports an associated manipulator 32, 34, which in turn movably supports an associated tool or an image capture device. Orienting platform 36 also supports an assistant display 31, which may be used for set-up, instrument changes, viewing of the procedure, and the like. The structures and use of any of the components of modular manipulator support assembly 30 are analogous to those described above regarding manipulator system 6, and are more fully described in co-pending U.S. patent application Ser. No. 11/043,688, filed on Jan. 24, 2005, and entitled "Modular Manipulator Support For Robotic Surgery", the full disclosure of which is incorporated herein by reference. Again, each manipulator 32, 34 may pass wireless communication signals therethrough in accordance with an embodiment of the present invention.

Referring now to FIGS. 5A through 5E, manipulator 8 including a telescopic insertion axis 100 is shown in more detail in accordance with an embodiment of the present invention. The insertion axis of the present invention is comprised of a 3-stage telescopic linear axis including three links, in one example, movably coupled to one another via rails, pulleys, and cables, with the links narrowing in width or form factor moving from the proximal link toward the distal link. Advantageously, the present invention provides for onehanded port and instrument clutching, a larger range of motion, a narrower insertion arm, and greater insertion axis stiffness and strength with reduced inertia as a function of insertion depth, thereby helping to enable a two-quadrant surgery with a single setup (e.g., a colorectal surgery), and providing for more space and visibility near the surgical field.

Figure 5B:
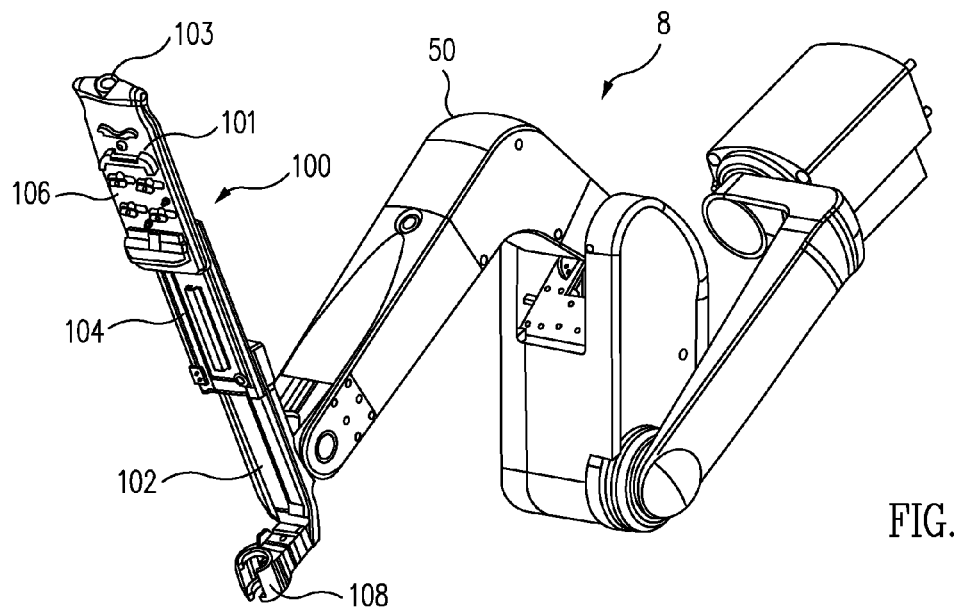
Figure 5C:
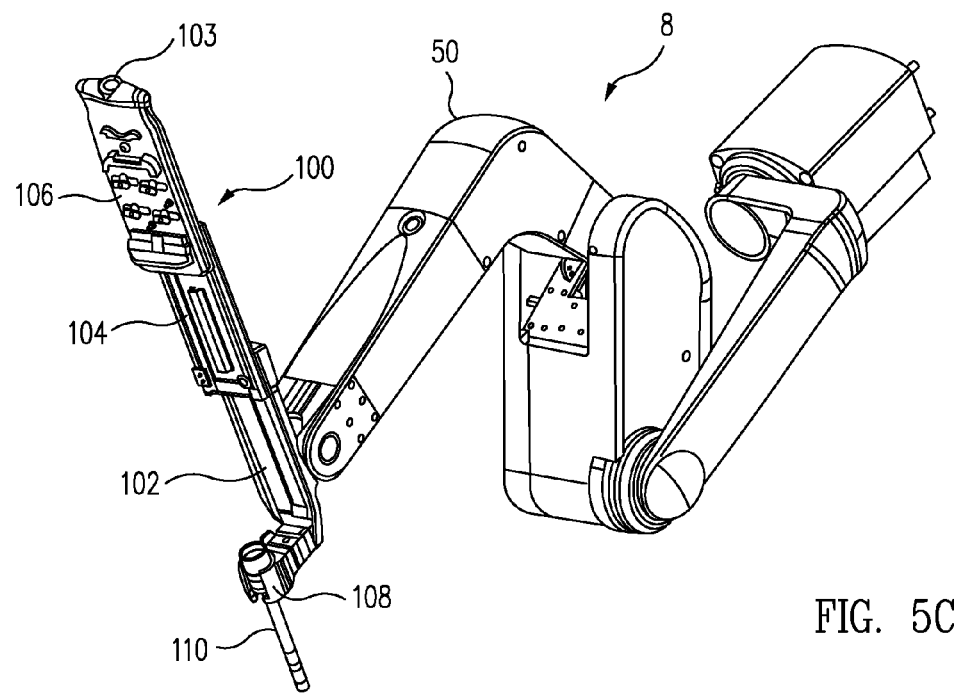
Figure 5D:
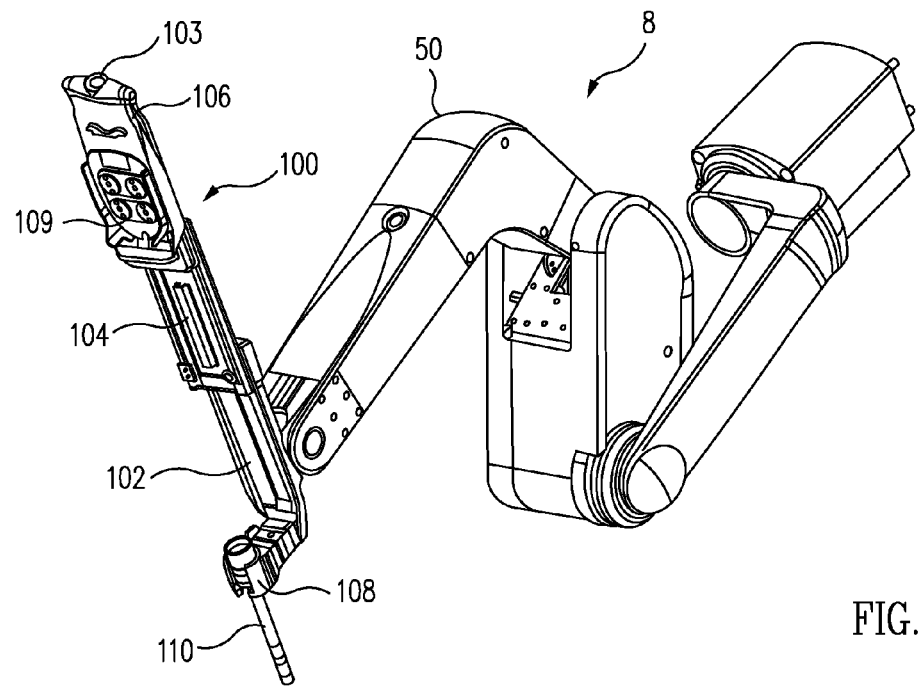
Figure 5E:
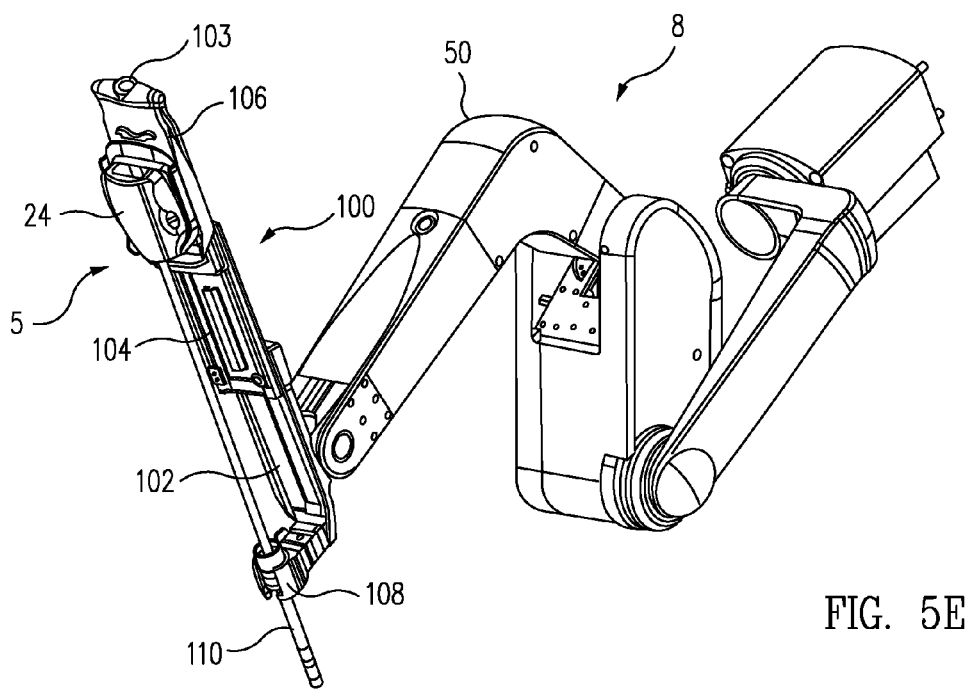

FIGS. 5A through 5E illustrate a perspective view of manipulator 8 including a manipulator arm 50, and telescopic insertion axis 100 operably coupled to a distal end of arm 50 in accordance with an embodiment of the present invention. Telescopic insertion axis 100 includes a first link or base link 102, a second link or idler link 104 operably coupled to base link 102, and a third link or carriage link 106 operably coupled to idler link 104. FIG. 5A1 illustrates a closer view of carriage link 106.

Base link 102 is operably coupled to a distal end of arm 50, and in one example has an accessory clamp 108 attached to a distal end of base link 102. An accessory 110, such as a cannula, may be mounted onto accessory clamp 108. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005, now U.S. Pat. No. 7,666,191, and in U.S. application Ser. No. 11/395,418, filed Mar. 31, 2006, now U.S. Pat. No. 7,699,855, the full disclosures of which are incorporated by reference herein for all purposes.

Carriage link 106 includes an instrument interface 101 for operably coupling to a sterile adaptor 109, which in turn is operably coupled to a housing 24 of an instrument 5, and controls the depth of the instrument inside a patient. In one embodiment, the sterile adaptor 109 may be part of a drape that may be draped over the robotic surgical system, and in particular the manipulator system, to establish a sterile barrier between the non-sterile PSM arms and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes.

Idler link 104 is movably coupled between base link 102 and carriage link 106 to allow the links 102, 104, and 106 to move relative to one another along a lengthwise axis (e.g., axis C) in a telescoping fashion.

Motion along axes A through G in manipulator 8, as shown in FIGS. 5A and 5A1, are provided by cables extending at least between the proximal and distal links in accordance with the present invention. The robotic arm can then control a tool operably coupled to the arm. The cables are a component of a transmission system also including drive pulleys, idler pulleys, and output pulleys, which are driven by electric motors. A pulley bank is located on an underside of base link 102 for passing cables between insertion axis 100 and manipulator arm 50 of manipulator system 6. A plurality of motion feedthroughs, in addition to other elements, may also be provided for transferring motion.

The drive assembly may further include a plurality of drive motors coupled to the arm for rotation therewith. Yaw and pitch motors control the motion of the arm about the A axis and the B axis (FIG. 5A), respectively, and drive motors control the motion of the wrist unit and surgical tool. In one embodiment, four drive motors are mounted proximally in the arm to control four degrees of freedom of the tool mounted distally on the arm (the D, E, F, and G axes). Also, a proximally mounted motor controls the insertion position of the tool distally on the arm (along the C axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which (including disclosures incorporated by reference therein) are incorporated herein by reference for all purposes. The manipulator arm and the drive assembly may also be used with a broad range of positioning devices. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes.

Prior robotic surgical systems have used electrical wire harnesses to provide power, ground, and/or data signals between the components of the surgical system. However, routing electrical cables or wire harnesses through the manipulator, in particular the insertion axis, may be disadvantageous for various reasons, including but not limited to insufficient space for the number of wires required, the bending required of the cable over its lifetime causing damage to the cable, surrounding parts of the robot being required to be enlarged to accommodate cables, and the cable not being sufficiently packaged out of the working area of the robot thereby causing disruption of the workflow and/or exposure of the cable to damage.

Figure 6:
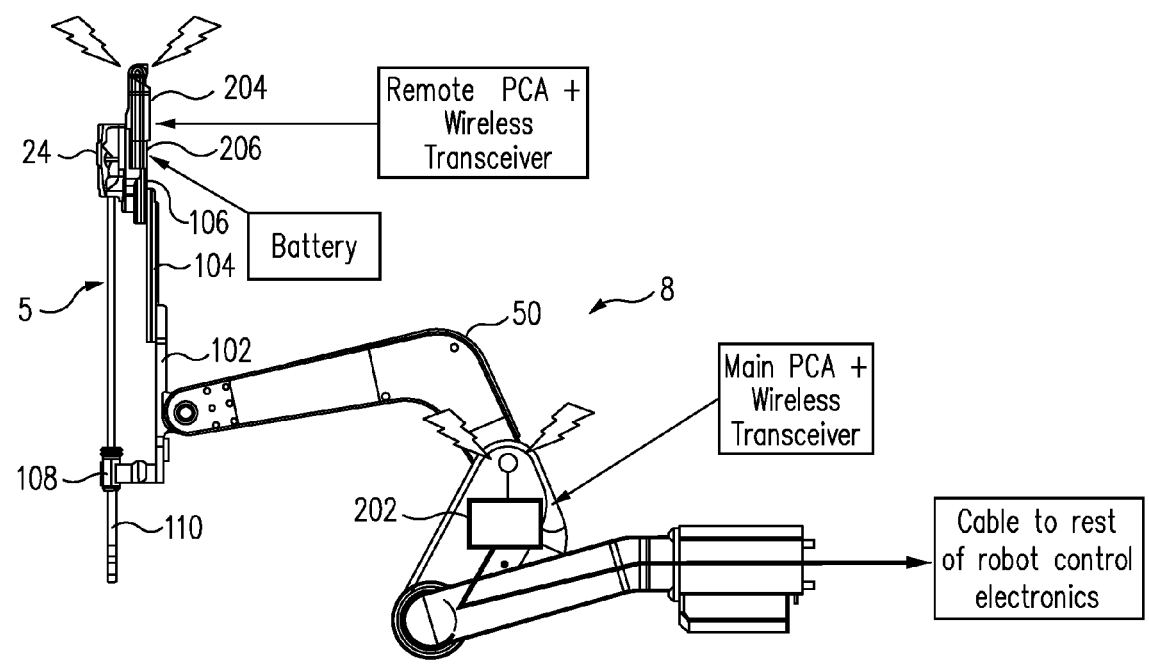
FIG. 6 is a side view of the manipulator of FIGS. 5A through 5E showing the wireless communication means and a power supply in accordance with an embodiment of the present invention.
Figure 7:
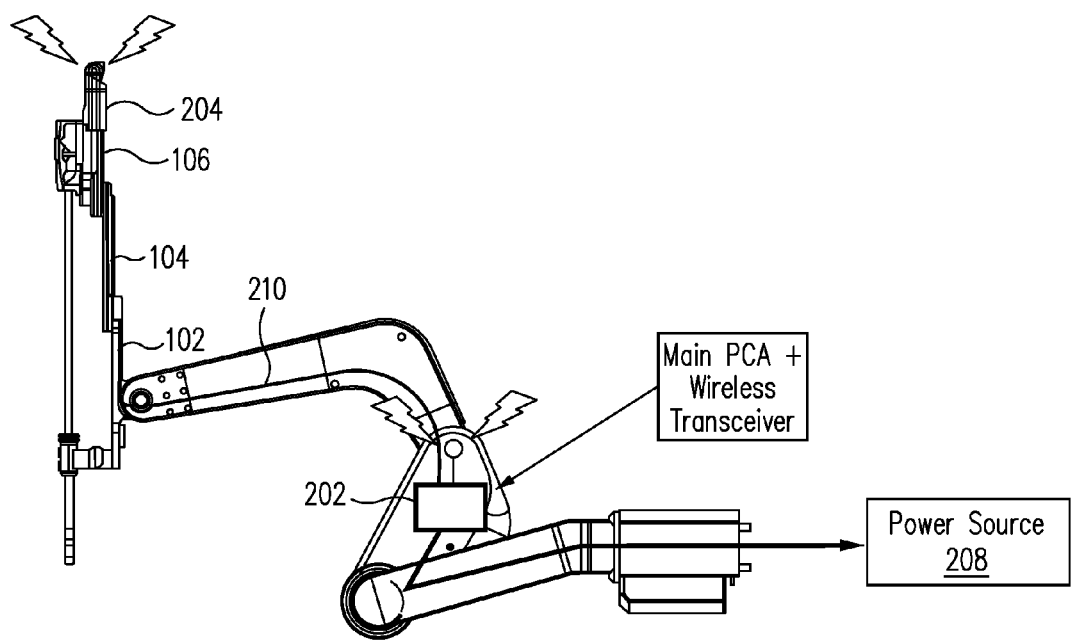
FIG. 7 is a side view of the manipulator of FIGS. 5A through 5E showing the wireless communication means and another power supply in accordance with another embodiment of the present invention.

Referring now to FIGS. 6 and 7 in conjunction with the earlier figures, a main printed circuit assembly (PCA) and wireless transceiver 202 ("main PCA/transceiver") and a remote PCA and wireless transceiver 204 ("remote PCA/transceiver") are used for wirelessly transferring data between a region of a surgical robot in accordance with an embodiment of the present invention.

In this embodiment, main PCA/transceiver 202 is located outside of insertion axis 100, in one example within a link of arm 50, and is operably coupled to other control electronics of the robotic surgical system. Remote PCA/transceiver 204 is located within insertion axis 100, in one example being within carriage link 106, and is operably coupled to interface 101 for receiving the sterile adaptor and the surgical instrument. In another example, remote PCA/transceiver 204 may be operably coupled to indicator 20. It is noted that the PCAs/transceivers 202 and 204 may be positioned in various locations of the surgical system, including a location external to the manipulator system, for allowing the wireless communication of data, and that multiple sets of main and remote PCAs/transceivers may also be used throughout the surgical system in accordance with an embodiment of the present invention.

Main PCA/transceiver 202 and remote PCA/transceiver 204 may support various wireless communication protocols, including but not limited to Bluetooth, IrDA, HomeRF, IEEE 802.11, DECT, and Wireless Telemetry. Data transmitted between remote PCA/transceiver 204 and main 202 may include information about the instrument (e.g., instrument identification, connection status to the sterile adaptor via a Hall Effect sensor, etc.), the sterile adaptor (e.g., connection status to the carriage link interface, etc.), and the state of the system (e.g., tissue manipulation mode, clutch mode, cannula presence, etc., that control for such things as LED color and blinking frequency). Thus, in one example, electrical signals may be communicated to and from a surgical tool, a sterile adaptor, LEDs, a clutch button, and Hall Effect sensors. Other examples of data are described in the User's Guide for the da Vinci® S™ surgical system available from Intuitive Surgical, Inc.

Figure 8A:
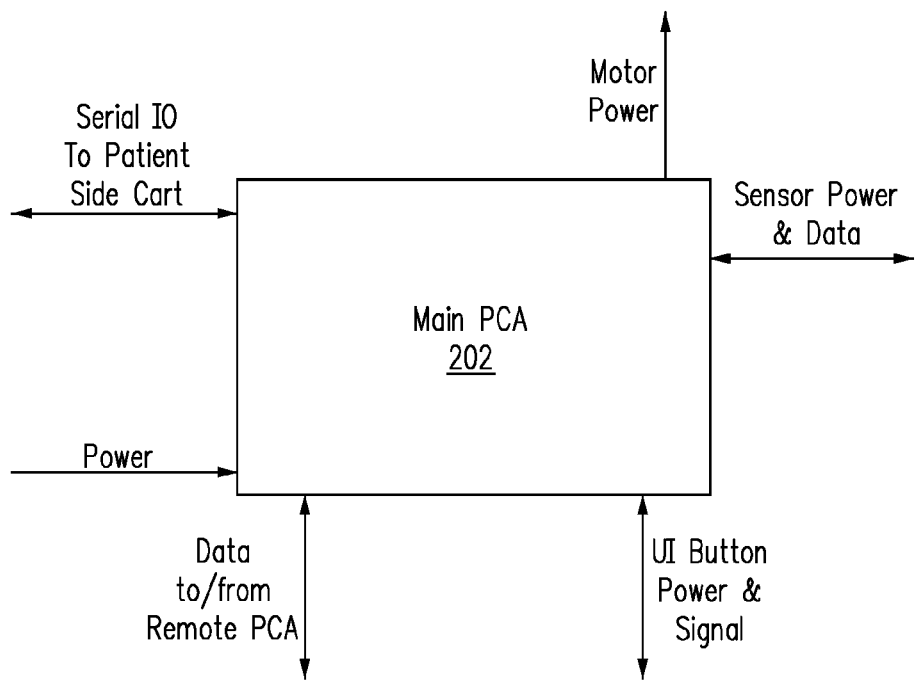
FIGS. 8A and 8B are block diagrams of a main printed circuit assembly (PCA) and a remote PCA, respectively, illustrating inputs and outputs of the PCAs.
Figure 8B:
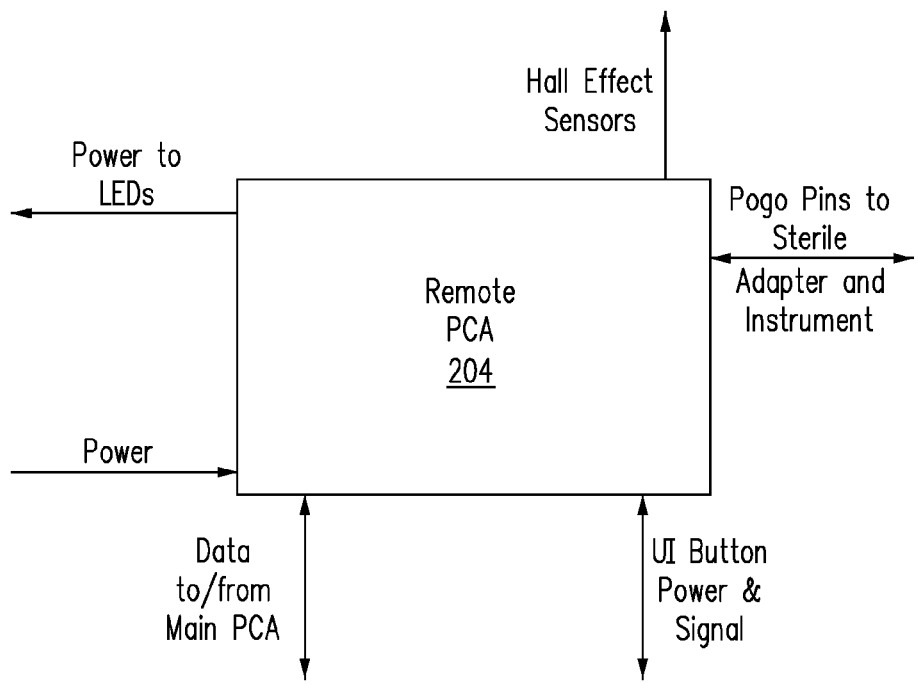

Referring now to FIGS. 8A and 8B, block diagrams of a main PCA 202 and a remote PCA 204, respectively, are illustrated showing inputs and outputs of the PCAs. In one embodiment, the remote PCA may have inputs and outputs for providing power and/or communicating with LEDs, Hall effect sensors, a sterile adaptor, an instrument, and a user interface button (e.g., for a clutch operation). The remote PCA may also include an input for receiving power and an input/output for communicating with a main PCA (e.g., processor 4 of FIG. 1). In one embodiment, the main PCA may have inputs and outputs for providing power and/or communicating with motors (e.g., the main PCA transmits position controls to the motors and processes potentiometer and encoder signals), sensors, the user interface button, the remote PCA, and other printed circuit boards on a patient side cart system via a serial communication bus. The remote PCA may include, in one example, an Embedded Serializer for Instrument Interface (ESII) PCA, and the main PCA may include, in one example, an Embedded Serializer Patient Manipulator (ESPM) PCA, both of which are available from Intuitive Surgical, Inc. of Sunnyvale, Calif. It is noted that other printed circuit assemblies or boards that allow for the communication of signals related to the instrument, the sterile adaptor, the accessory, and/or the state of the system are within the scope of the present invention.

In other embodiments, data transmission (including across a sterile drape) may be by optical, close-coupled magnetics, and/or radio wave transmission. In optical transmissions, data may be communicated using modulated light emitters, LEDS, lasers, and/or an optical sensor. Magnetic coupling of data may be accomplished via primary and secondary parts of a transformer.

In accordance with another embodiment of the present invention, various means for providing power to the remote PCA/transceiver 204 are disclosed. In one example, a battery 206 is operably coupled to remote PCA/transceiver 204. For the case of low power consumption, a small disposable battery may be used to power the remote PCA/transceiver 204. Field service personnel may preemptively change this battery a few times a year. For higher power consumption cases, such as for providing power to LEDs of the insertion axis indicators 20 (FIGS. 1 and 2), rechargeable batteries may be utilized. In one example, an inductive charging system may be used such that the battery for the remote PCA may be charged when the system is not in use (e.g., the insertion axis may completely retract when the system is turned off thereby bringing charger coils sufficiently close to charge the battery). Advantageously, no conductors are exposed and no batteries need be replaced in this embodiment. In a further embodiment, a large battery on the manipulator cart can charge the remote PCA battery even if the cart is not plugged into a wall socket.

In another example for providing power to the remote PCA/transceiver, a wire 210 may be routed to the remote PCA 204 to provide power from a power source 208 external to the insertion axis, thereby eliminating many of the wires between the two PCAs/transceivers.

Figure 9A:
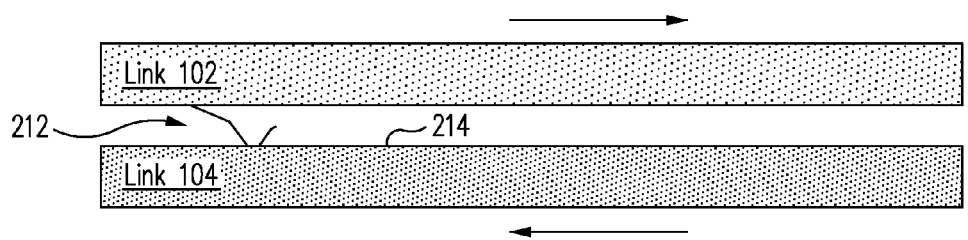
FIGS. 9A and 9B are simple block diagrams showing a sliding brush contact for providing power to a wireless communication means in accordance with an embodiment of the present invention.
Figure 9B:
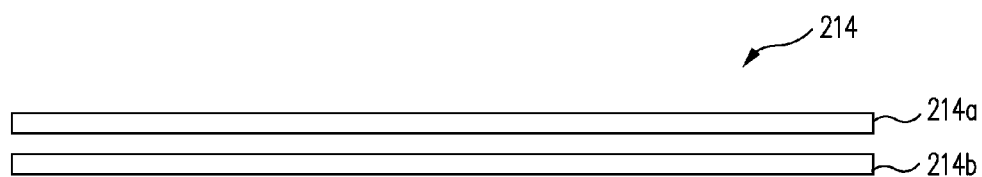

In yet another example for providing power, sliding wiper contacts may be used between the base link 102 and idler link 104, and between the idler link 104 and the carriage link 106. FIGS. 9A and 9B illustrate an example of sliding wiper contacts between links 102 and 104. Substantially similar structures could be used between links 104 and 106. FIG. 9A illustrates a simplified side view of a conductive brush 212 attached to link 102 (or alternatively on link 104) that slides over a conductive lengthwise track 214 on link 104 (or alternatively on link 102) and that allows for electrical coupling between links 102 and 104 even during relative movement of the links. FIG. 9B illustrates a simplified top view of the lengthwise track 214 that may include two parallel tracks 214a and 214b, with one track for power and the other track for ground. Brush 212 may be preloaded against track 214 to ensure good contact in one example.

In yet another example of providing power transmission, AC magnetic coupling of separated primary and secondary structures of a transformer may be used. The transformer may be wound with wire or printed circuit traces, and switching power circuits may be used to provide isolated power.

Advantageously, electrical cables may be substantially eliminated between the main PCA and the remote PCA, thereby enabling the surgical manipulator to be made smaller and to perform with less potential for failure from complications related to cable/wire failure. Furthermore, separation of the electrical circuits provides a barrier to leakage currents that might otherwise cause electrical harm to patients and/or medical staff.

Embodiments described above illustrate but do not limit the invention. It should also be understood that numerous modifications and variations are possible in accordance with the principles of the present invention. For example, numerous PCAs and respective transceivers placed in various system locations is within the scope of the present invention. Furthermore, the system is not limited to four robotic manipulator assemblies, but may include two or more in other examples. Accordingly, the scope of the invention is defined only by the following claims.

We claim:

1. A link assembly of a robotic manipulator, comprising:
  a base link operably coupled to a distal end of a manipulator arm, wherein the base link includes a clamp adapted to mount a cannula;
  an idler link slidably coupled to the base link along a lengthwise axis of the link assembly; and
  a carriage link slidably coupled to the idler link along the lengthwise axis,
  wherein the carriage link includes an instrument interface adapted to mount an instrument having an instrument shaft,
  wherein the carriage link and the idler link are configured for telescoping motion relative to the base link to move a distal end of the instrument shaft relative to the clamp, and
  wherein the carriage link includes a remote printed circuit assembly, a power source for the remote printed circuit assembly, and a transceiver for wirelessly communicating with a main printed circuit assembly external to the link assembly.

2. The link assembly of claim 1, wherein the remote printed circuit assembly and transceiver transmit data selected from the group consisting of a system state, a sterile adaptor state, and an instrument state.

3. The link assembly of claim 1, wherein the remote printed circuit assembly and transceiver transmit data selected from the group consisting of instrument identification, LED control, clutch button state, and Hall-effect sensor state.

4. The link assembly of claim 1, wherein the carriage link includes an LED indicator, and a manipulator clutch button.

5. The link assembly of claim 1, wherein the instrument interface is capable of mounting an instrument having an end effector selected from the group consisting of jaws, scissors, graspers, needle holders, micro-dissectors, staple appliers, tackers, suction irrigation tools, clip appliers, cutting blades, cautery probes, irrigators, catheters, and suction orifices.

6. The link assembly of claim 1, wherein the power source includes a battery selected from the group consisting of a rechargeable battery and a disposable battery.

7. A link assembly of a robotic manipulator, comprising:
a base link operably coupled to a distal end of a manipulator arm, wherein the base link includes a clamp adapted to mount a cannula;
an idler link slidably coupled to the base link along a lengthwise axis of the link assembly; and
a carriage link slidably coupled to the idler link along the lengthwise axis,
wherein the carriage link includes an instrument interface adapted to mount an instrument having an instrument shaft,
wherein the carriage link and the idler link are configured for telescoping motion relative to the base link to move a distal end of the instrument shaft relative to the clamp,
wherein the carriage link includes a remote printed circuit assembly and transceiver for wirelessly communicating with a main printed circuit assembly external to the link assembly, and
wherein the remote printed circuit assembly is coupled by a wire to a power source external to the link assembly.

8. A link assembly of a robotic manipulator, comprising:
a base link operably coupled to a distal end of a manipulator arm, wherein the base link includes a clamp adapted to mount a cannula;
an idler link slidably coupled to the base link along a lengthwise axis of the link assembly; and
a carriage link slidably coupled to the idler link along the lengthwise axis,
wherein the carriage link includes an instrument interface adapted to mount an instrument having an instrument shaft,
wherein the carriage link and the idler link are configured for telescoping motion relative to the base link to move a distal end of the instrument shaft relative to the clamp,
wherein the carriage link includes a remote printed circuit assembly and transceiver for wirelessly communicating with a main printed circuit assembly external to the link assembly, and
wherein a contact brush and a contact track apparatus is between the base link and the carriage link for providing power to the remote printed circuit assembly from a remote power source outside of the link assembly.

9. A robotic surgical manipulator system, comprising:
a manipulator arm including a main printed circuit assembly and transceiver;
a link assembly operably coupled to a distal end of the manipulator arm, the link assembly including:
a base link having a clamp adapted to mount a cannula,
an idler link slidably coupled to the base link along a lengthwise axis of the link assembly, and
a carriage link slidably coupled to the idler link along the lengthwise axis, the carriage link including an instrument interface, a remote printed circuit assembly, a power source for the remote printed circuit assembly, and a transceiver for wirelessly communicating with the main printed circuit assembly, wherein the instrument interface is adapted to mount an instrument having an instrument shaft, and wherein the carriage link and the idler link are configured for telescoping motion relative to the base link to move a distal end of the instrument shaft relative to the clamp;
a sterile adaptor coupled to the instrument interface; and
an instrument coupled to the sterile adapter, wherein the remote printed circuit assembly and transceiver wirelessly transmit data of a sterile adaptor state and an instrument state to the main printed circuit assembly.

10. The system of claim 9, wherein the remote printed circuit assembly and transceiver transmit data including a system state.

11. The system in of claim 9, wherein the carriage link includes an LED indicator and a manipulator clutch button.

12. The system of claim 9, wherein the instrument includes an end effector selected from the group consisting of jaws, scissors, graspers, needle holders, micro-dissectors, staple appliers, tackers, suction irrigation tools, clip appliers, cutting blades, cautery probes, irrigators, catheters, and suction orifices.

13. The system of claim 9, wherein the power source includes a battery selected from the group consisting of a rechargeable battery and a disposable battery.

14. The system of claim 9, wherein the sterile adaptor is operably coupled between the instrument interface and the instrument.

15. A robotic surgical manipulator system, comprising:
a manipulator arm including a main printed circuit assembly and transceiver;
a link assembly operably coupled to a distal end of the manipulator arm, the link assembly including:
a base link having a clamp adapted to mount a cannula,
an idler link slidably coupled to the base link along a lengthwise axis of the link assembly, and
a carriage link slidably coupled to the idler link along the lengthwise axis, the carriage link including an instrument interface, and a remote printed circuit assembly and transceiver for wirelessly communicating with the main printed circuit assembly, wherein the instrument interface is adapted to mount an instrument having an instrument shaft, wherein the remote printed circuit assembly is coupled by a wire to a remote power source outside of the link assembly, and wherein the carriage link and the idler link are configured for telescoping motion relative to the base link to move a distal end of the instrument shaft relative to the clamp;
a sterile adaptor coupled to the instrument interface; and
an instrument coupled to the sterile adapter, wherein the remote printed circuit assembly and transceiver wirelessly transmit data of a sterile adaptor state and an instrument state to the main printed circuit assembly.

16. A robotic surgical manipulator system, comprising:
a manipulator arm including a main printed circuit assembly and transceiver;
a link assembly operably coupled to a distal end of the manipulator arm, the link assembly including:
a base link having a clamp adapted to mount a cannula,
an idler link slidably coupled to the base link along a lengthwise axis of the link assembly,
a carriage link slidably coupled to the idler link along the lengthwise axis, the carriage link including an instrument interface, and a remote printed circuit assembly and transceiver for wirelessly communicating with the main printed circuit assembly, wherein the instrument interface is adapted to mount an instrument having an instrument shaft, and wherein the carriage link and the idler link are configured for telescoping motion relative to the base link to move a distal end of the instrument shaft relative to the clamp, and
a contact brush and a contact track apparatus between the base link and the carriage link for providing power to the remote printed circuit assembly from a remote power source outside of the link assembly;

a sterile adaptor coupled to the instrument interface; and
an instrument coupled to the sterile adapter, wherein the remote printed circuit assembly and transceiver wirelessly transmit data of a sterile adaptor state and an instrument state to the main printed circuit assembly.

17. A method of wireless communication in a robotic surgical system, comprising:
providing a manipulator arm including a main printed circuit assembly and transceiver;
providing a link assembly operably coupled to a distal end of the manipulator arm, the link assembly including:
a base link having a clamp adapted to mount a cannula,
an idler link slidably coupled to the base link along a lengthwise axis of the link assembly, and
a carriage link slidably coupled to the idler link along the lengthwise axis, the carriage link including an instrument interface and a remote printed circuit assembly and transceiver, wherein the instrument interface is adapted to mount an instrument having an instrument shaft, and wherein the carriage link and the idler link are configured for telescoping motion relative to the base link to move a distal end of the instrument shaft relative to the clamp;
coupling a sterile adaptor to the instrument interface;
coupling an instrument to the sterile adaptor;
powering the remote printed circuit assembly with a power source external or internal to the link assembly; and
transmitting data of a sterile adaptor state and an instrument state wirelessly from the remote printed circuit assembly to the main printed circuit assembly.

18. The method of claim 17, wherein the transmitted data includes a system state.

19. The method of claim 17, further comprising powering the remote printed circuit assembly with a power source including a battery selected from the group consisting of a rechargeable battery and a disposable battery.

* * * * *